United States Patent
Carls

(10) Patent No.: US 9,844,397 B2
(45) Date of Patent: Dec. 19, 2017

(54) SPINAL CORRECTION SYSTEM AND METHOD

(71) Applicant: Warsaw Orthopedic, Inc., Warsaw, IN (US)

(72) Inventor: Thomas A. Carls, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 149 days.

(21) Appl. No.: 14/692,932

(22) Filed: Apr. 22, 2015

(65) Prior Publication Data

US 2016/0310170 A1  Oct. 27, 2016

(51) Int. Cl.
*A61B 17/70* (2006.01)

(52) U.S. Cl.
CPC ........ *A61B 17/7022* (2013.01); *A61B 17/701* (2013.01); *A61B 17/7038* (2013.01); *A61B 17/7046* (2013.01); *A61B 17/7032* (2013.01)

(58) Field of Classification Search
CPC .............. A61B 17/7014; A61B 17/701; A61B 17/7022; A61B 17/7032; A61B 17/7037
USPC ....... 606/246, 254, 255, 257, 261, 263, 264, 606/265, 270, 279
See application file for complete search history.

(56) References Cited

U.S. PATENT DOCUMENTS

| | | | | |
|---|---|---|---|---|
| 4,369,769 A * | 1/1983 | Edwards | ............ | A61B 17/7001 606/257 |
| 5,282,863 A * | 2/1994 | Burton | ............... | A61B 17/7007 606/254 |
| 7,125,410 B2 * | 10/2006 | Freudiger | .......... | A61B 17/7005 606/254 |
| 7,824,430 B2 * | 11/2010 | Allard | ................ | A61B 17/7022 606/279 |
| 2007/0129729 A1 * | 6/2007 | Petit | ................... | A61B 17/7031 606/254 |
| 2009/0131982 A1 * | 5/2009 | Schwab | ............. | A61B 17/7001 606/246 |
| 2014/0094851 A1 * | 4/2014 | Gordon | .............. | A61B 17/7001 606/264 |
| 2015/0164561 A1 * | 6/2015 | Simpson | ............ | A61B 17/7002 606/264 |

* cited by examiner

*Primary Examiner* — Pedro Philogene
*Assistant Examiner* — David C Comstock

(57) ABSTRACT

A spinal construct comprises a first member configured for attachment to a first portion of vertebral tissue that defines a longitudinal axis. A second member is configured for attachment to a second portion of the vertebral tissue such that the second portion is axially movable relative to the second member and sagittal movement of the second member relative to the second portion is resisted and/or prevented. Systems and methods are disclosed.

20 Claims, 7 Drawing Sheets

SPINAL CORRECTION SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, bone screws and sub-laminar wire, for stabilization of a treated section of a spine. This disclosure describes an improvement over these prior art technologies.

SUMMARY

In one embodiment, a spinal construct is provided. The spinal construct comprises a first member configured for attachment to a first portion of vertebral tissue that defines a longitudinal axis. A second member is configured for attachment to a second portion of the vertebral tissue such that the second portion is axially movable relative to the second member and sagittal movement of the second member relative to the second portion is resisted and/or prevented. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
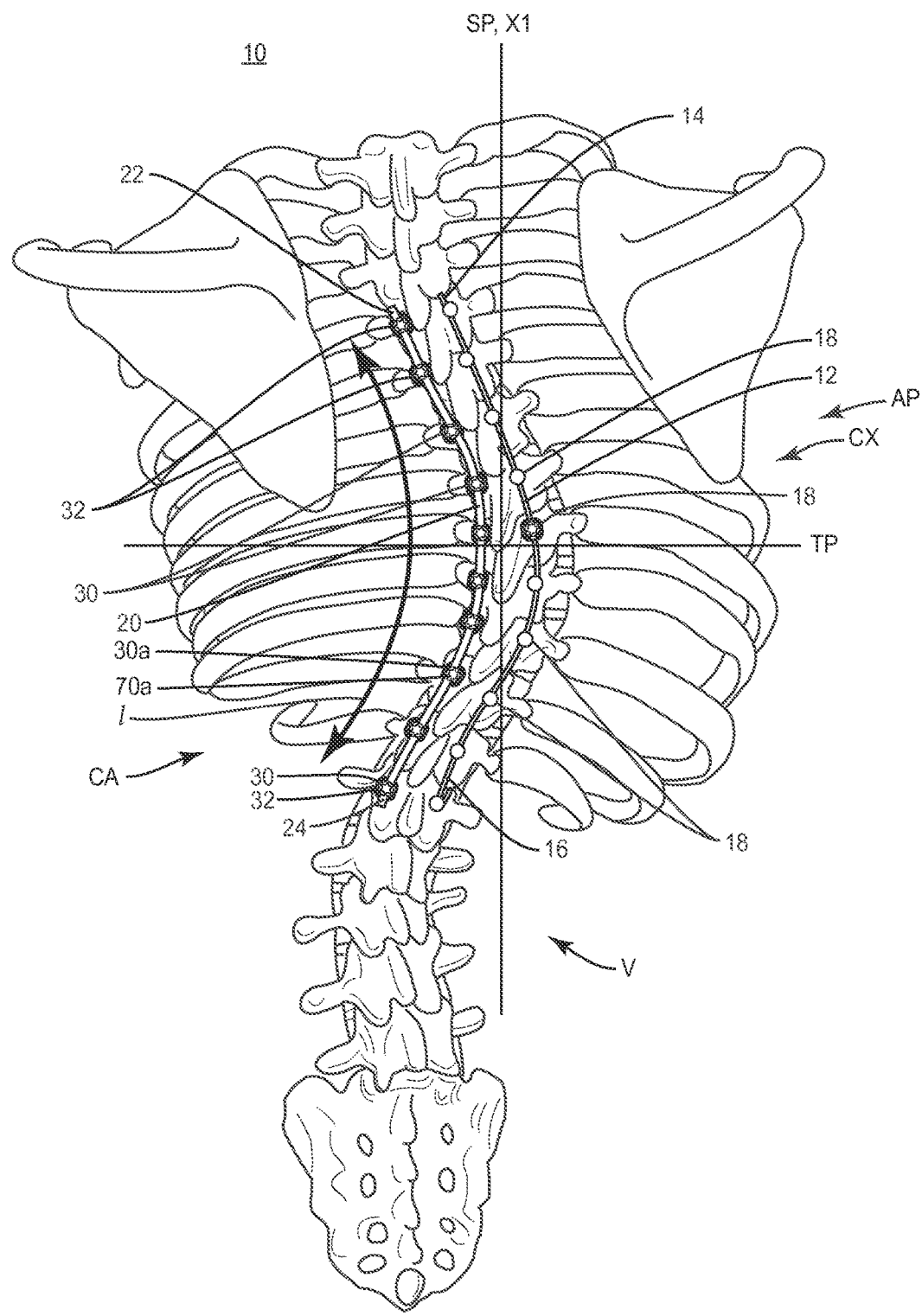
FIG. 1 is a plan view of one embodiment of components of a surgical system in accordance with the principles of the present disclosure disposed with vertebrae.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis.

In some embodiments, the surgical system includes a spinal implant, such as, for example, a tether on a convex side of a spine for constraining growth and a spinal implant, such as, for example, a longitudinal rod on a concave side of a spine to direct growth for correction of idiopathic scoliosis. In some embodiments, the surgical system includes a semi-rigid, longitudinal rod construct. In some embodiments, the longitudinal rod may include a thickness to provide more flexibility in one direction than in a second direction. In some embodiments, the longitudinal rod is configured to prevent lordosis in a sagittal plane of a thoracic spine. In some embodiments, the longitudinal rod is attached with a connector such that the longitudinal rod and connector interface is mostly rigid in a sagittal plane and flexible in a coronal plane to facilitate correction of a lateral deformity of the spine and maintain a selected sagittal curve. In some embodiments, the surgical system includes a longitudinal rod and connector construct configured to be rigid in the sagittal plane and facilitates rotation in the axial plane. In some embodiments, the longitudinal rod includes a selected curvature for a patient. In some embodiments, the surgical system includes a longitudinal rod configured to prevent rotation when disposed with a connector.

In some embodiments, the surgical system includes a longitudinal rod having a non-circular cross-section, such as, for example, oblong or elliptical. In some embodiments, the surgical system includes a longitudinal rod that is flexible along a first dimension and rigid along a greater, second dimension. In some embodiments, the longitudinal rod does not rotate about itself when disposed with a connector. In some embodiments, the surgical system includes a bone fastener having a pivot mechanism.

In some embodiments, the surgical system is configured to prevent lordosis of a thoracic spine as a patient grows. In some embodiments, the surgical system includes a guided growth rigid rod system disposed with a concave thoracic portion of the spine and a tether system disposed with a convex portion of the spine. In some embodiments, the tether is connected with a spine for growth modulation and supported by a longitudinal rod. In some embodiments, the surgical system includes a pedicle screw and a set screw for fixing the tether with the spine. In some embodiments, the guided growth rigid rod system includes a bone fastener, such as, for example, a pedicle screw and a rod securing member, such as, for example, a set screw. In some embodiments, the set screw is configured for rigid fixation, for example, at the APEX of the concave curve. In some embodiments, the set screw is configured as a non-rod locking set screw, such as, for example, a growth rod set screw. In some embodiments, the non-locking rod set screw facilitates movement of the rod relative to the bone fastener.

In some embodiments, the surgical system includes a guided growth rigid rod configured to prevent movement and/or is rigid in the sagittal plane. In some embodiments, the surgical system includes a guided growth rigid rod configured to prevent movement and/or is rigid in the coronal plane. In some embodiments, the surgical system includes a guided growth rod that is flexible and configured to facilitate movement and/or is flexible in the coronal plane.

In some embodiments, the surgical system comprises a dynamic rod capture system including a multi-axial fastener. In some embodiments, the surgical system includes a fixed axis fastener. In some embodiments, the surgical system includes a hinged fixed axial fastener. In some embodiments, the fasteners are configured to facilitate movement between the fastener and the rod in a superior and/or an inferior direction. In some embodiments, the fasteners are configured to facilitate movement between the fastener and the rod in an axial direction. In some embodiments, the fasteners are configured to limit movement between the fastener and the rod in the anterior direction and/or posterior direction.

In some embodiments, the surgical system is utilized with a method including the steps of placing a tether and fastener system on a convex side of a spine; placing fasteners on a concave side of a spine; engaging fastener heads that are free to rotate in an axial plane of each vertebral body; and placing a rod into the heads and securing the rod with a set screw.

In some embodiments, the surgical system is configured to facilitate straightening of a coronal curve on the convex side of a spine. In some embodiments, the surgical system employs a sagittally rigid rod, which is pre-bent or machined with a thoracic curve to resist a lordosing force applied by growth to the thoracic spine along the concave portion of the spine. In some embodiments, the rod is configured to facilitate growth in other directions by not fixing the rod with the fastener to allow axial translation from vertebra to vertebra along the rod. In some embodiments, the surgical system includes axial rotating fastener heads that allow vertebrae to rotate axially relative to the rod causing rigidity in the sagittal plane that is stiffer than in the coronal plane. This configuration facilitates a sagittal curve of kyphosis while allowing the rod to bend in the coronal plane.

In some embodiments, a fastener and a rod are fixed at a middle point of the spinal construct along the spine to maintain the rod fixed in place while allowing other vertebral bodies to move relative to a fixed rod portion.

In some embodiments, the surgical system is used with surgical navigation, such as, for example, fluoroscope or image guidance. In one embodiment, one or all of the components of the surgical system are disposable, peel-pack, pre-packed sterile devices. One or all of the components of the surgical system may be reusable. The surgical system may be configured as a kit with multiple sized and configured components.

In one embodiment, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one embodiment, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
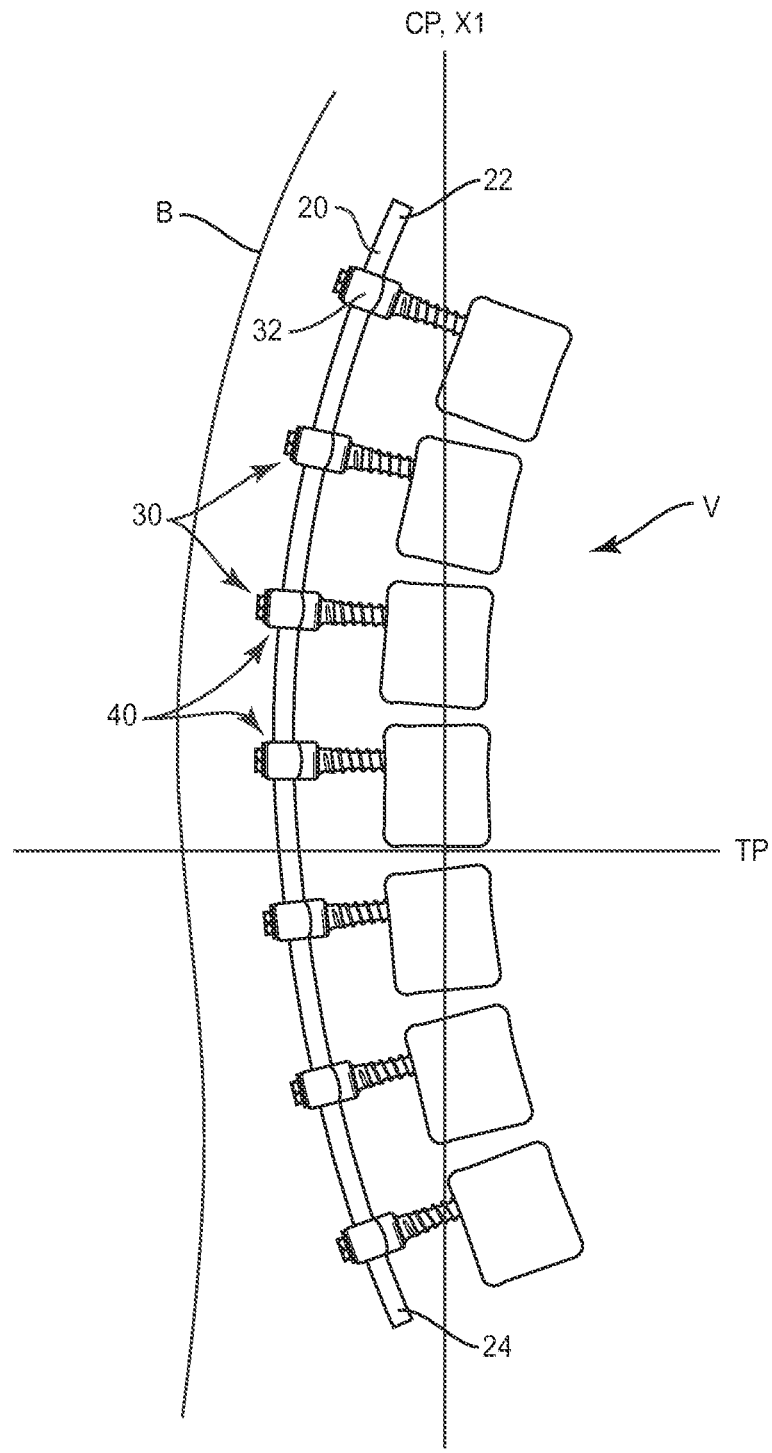
FIG. 2 is a side sagittal view of the components and vertebrae shown in FIG. 1.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1 and 2, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tricalcium phosphate (TCP), HA-TCP, calcium sulfate, or other resorbable polymers such as poly-aetide, polyglycolide, polytyrosine carbonate, polycaropla-etohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 comprises a member, such as, for example, a tether 12. Tether 12 is a flexible longitudinal element that extends between an end 14 and an end 16. Tether 12 is configured for connection with a portion of vertebral tissue, such as, for example, a convex side CX of vertebrae V, which defines a longitudinal axis X1, with fasteners, such as, for example, bone screws 18. Tether 12 is configured for tensioning a targeted portion of vertebrae V, as described herein. In some embodiments, tether 12 tensions a targeted portion of vertebrae V to constrain growth and a longitudinal rod guides growth, as described herein. In some embodiments, the targeted portion of vertebrae V may include laminae, transverse process and/or pedicle regions of one or a plurality of vertebral levels. In some embodiments, spinal correction system 10 may include one or a plurality of tethers 12.

Tether 12 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of tether 12 allows movement in a lateral or side to side direction and prevents expanding and/or extension in an axial direction upon tensioning and attachment with a targeted portion of an anatomy. In some embodiments, all or only a portion of tether 12 may have a semi-rigid, rigid or elastic configuration, and/or have elastic properties, similar to the material examples described above, such that tether 12 provides a selective amount of expansion and/or extension in an axial direction. In some embodiments, tether 12 may be compressible in an axial direction. Tether 12 can include a plurality of separately attachable or connectable portions or sections, such as bands or loops, or may be monolithically formed as a single continuous element.

Tether 12 can have a uniform thickness/diameter. In some embodiments, tether 12 may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 12 may be uniformly increasing or decreasing, or have alternate diameter dimensions along its length. In some embodiments, tether 12 may have various cross section configurations, such as, for example, oval, oblong, triangular, rectangular, square, polygonal, irregular, uniform, non-uniform, variable and/or tapered. In some embodiments, the surface of tether 12 may include engaging structures, such as, for example, barbs, raised elements and/or spikes to facilitate engagement with tissue of a targeted anatomy.

In some embodiments, tether 12 may have various lengths. In some embodiments, tether 12 may be braided, such as a rope, or include a plurality elongated elements to provide a predetermined force resistance. In some embodiments, tether 12 may be made from autograft and/or allograft, and be configured for resorbable or degradable applications. In one embodiment, tether 12 is a cadaver tendon. In one embodiment, tether 12 is a tendon that may be harvested, for example, from a patient or donor. In some embodiments, a tendon harvested from a patient may be affixed in remote locations with the patient's body.

Figure 3:
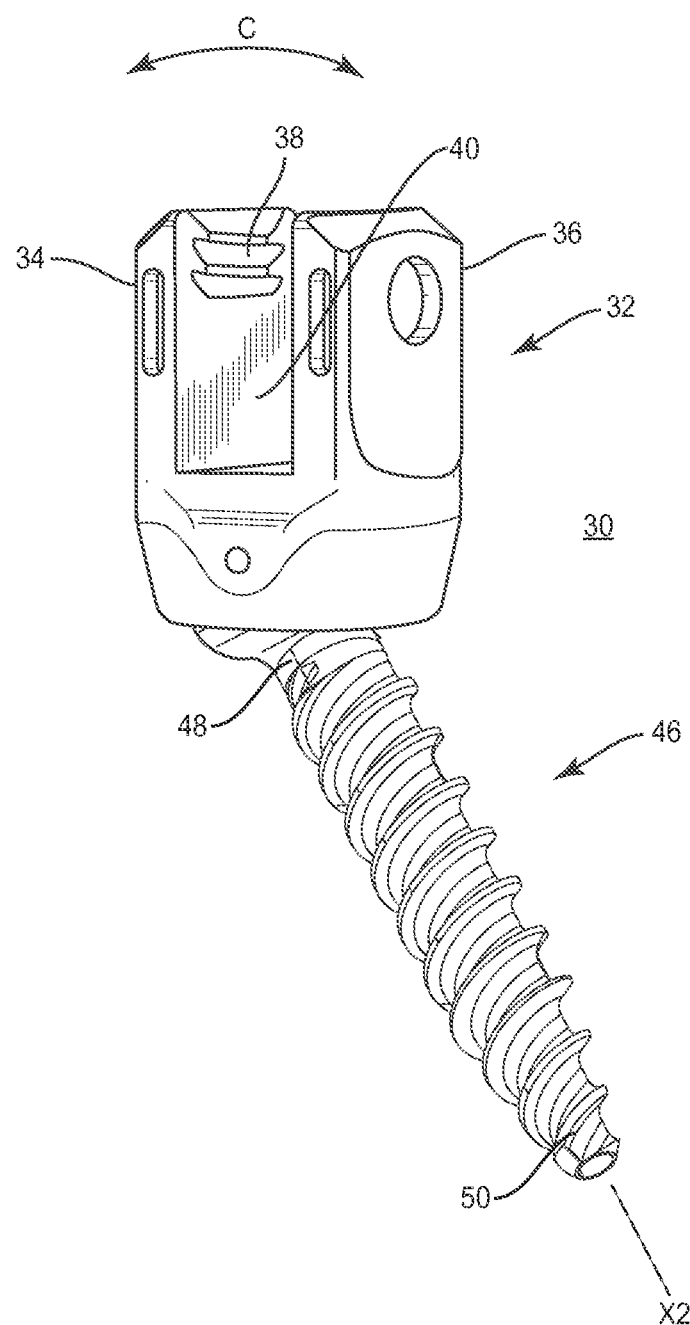
FIG. 3 is a perspective view of one embodiment of components of a surgical system in accordance with the principles of the present disclosure.

Spinal correction system 10 includes a member, such as, for example, a longitudinal rod 20, as shown in FIGS. 1, 2, 4 and 5. Longitudinal rod 20 extends between an end 22 and an end 24. Longitudinal rod 20 is configured for connection to a portion of vertebral tissue, such as, for example, a concave side CA of vertebrae V. Longitudinal rod 20 has a length l that extends axially along vertebrae V of body B. In some embodiments, longitudinal rod 20 attaches to concave side CA with fasteners, such as, for example, pedicle screws 30, as shown in FIG. 3. In some embodiments, longitudinal rod 20 is flexible along a coronal plane CP relative to concave side CA to facilitate growth of vertebrae V. In some embodiments, longitudinal rod 20 is configured to resist and/or prevent movement of vertebrae V in a sagittal plane SP relative to concave side CA to prevent lordosis of the spine during growth.

Figure 4:
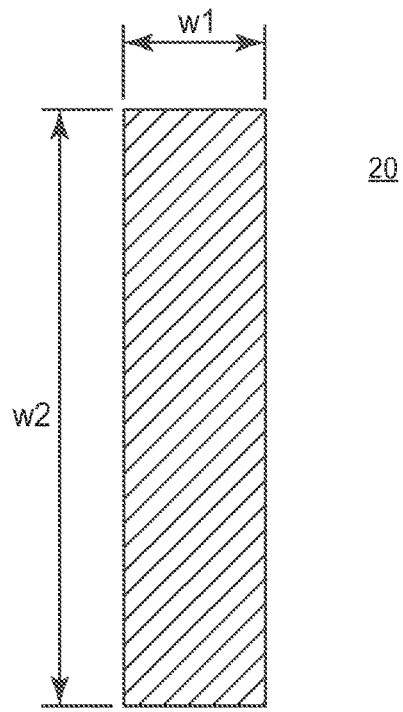
FIG. 4 is cross-section view of one embodiment of a component of a surgical system in accordance with the principles of the present disclosure.
Figure 4A:
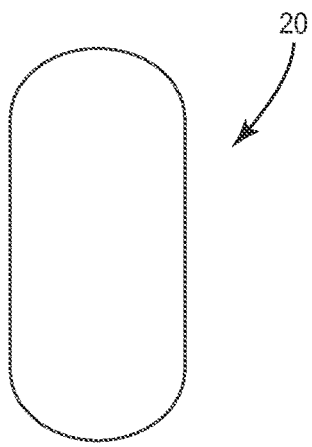
FIG. 4A is cross-section view of one embodiment of a component of a surgical system in accordance with the principles of the present disclosure.
Figure 4B:
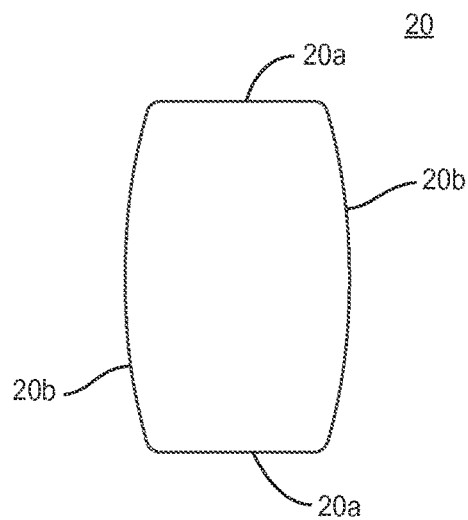
FIG. 4B is cross-section view of one embodiment of a component of a surgical system in accordance with the principles of the present disclosure.
Figure 5:
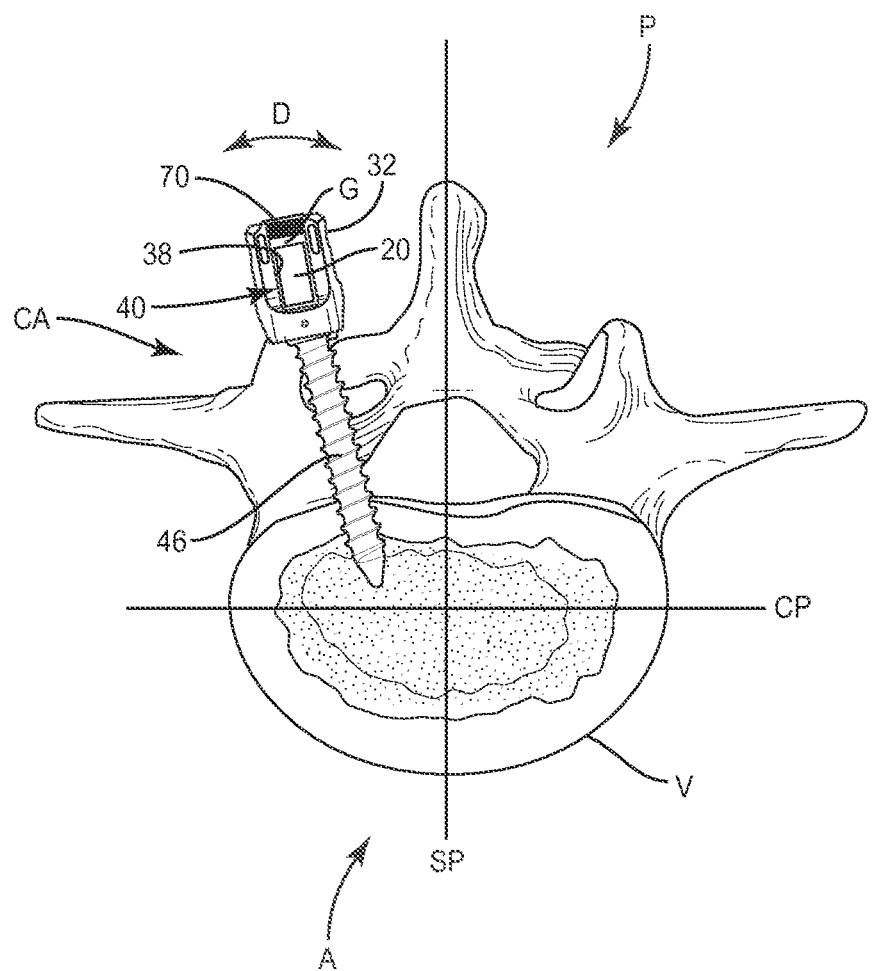
FIG. 5 is a plan transverse/axial view of one embodiment of components of a surgical system in accordance with the principles of the present disclosure disposed with vertebrae.

Longitudinal rod 20 has a cross-section having a width w1 and a width w2 having a greater dimension than width w1, as shown in FIG. 4. In one embodiment, as shown in FIG. 4A, longitudinal rod 20 has an oblong cross-section configuration. In one embodiment, as shown in FIG. 4B, longitudinal rod 20 has an oblong configuration including linear sides 20a and arcuate sides 20b. Longitudinal rod 20 is connected with concave side CA, as shown in FIG. 5, and width w1 extends medial-lateral and width w2 extends anterior A-posterior P relative to vertebrae V. Width w1 is configured to facilitate movement, rotation and/or flexibility of longitudinal rod 20 in coronal plane CP. Width w2 is configured to resist and/or prevent movement, rotation and/or flexibility of longitudinal rod 20 in sagittal plane SP.

In some embodiments, width w1 includes a thickness to provide flexibility in a first direction and width w2 includes a thickness to resist and/or prevent flexibility in a second direction. In some embodiments, the configuration of width w1 and width w2 resists and/or prevents lordosis in a sagittal plane of a thoracic spine. In some embodiments, the configuration of width w1 and width w2 maintains a selected kyphotic curve of vertebrae V in a sagittal plane of a thoracic spine. In some embodiments, system 10 comprises a spinal construct including longitudinal rod 20 attached with a connector (not shown) such that the spinal construct is rigid in a sagittal plane and flexible in a coronal plane to facilitate correction of a lateral deformity of vertebrae V and maintain a selected sagittal curve. In some embodiments, spinal correction system 10 includes longitudinal rod 20 and a connector construct configured to be rigid in the sagittal plane and facilitates rotation in the coronal plane.

In some embodiments, longitudinal rod 20 includes a pre-selected curvature having a selected kyphotic curve, which may include curvature in a sagittal plane of a thoracic spine. As such, width w1 and width w2 allow longitudinal rod 20 to maintain a selected kyphotic sagittal curve as vertebrae V grows by allowing flexibility in coronal plane CP and resisting and/or preventing movement in sagittal plane SP. In some embodiments, longitudinal rod 20 includes a pre-selected curvature that applies a force to resist and/or prevent lordosis of vertebrae V from the components of spinal correction system 10 as vertebrae V grows.

In some embodiments, longitudinal rod 20 can be disposed co-axial, offset, staggered, transverse, angular and/or relative posterior/anterior orientations relative to tether 12. In some embodiments, longitudinal rod 20 has a rigid and/or non-flexible configuration relative to tether 12 such that all or only a portion of longitudinal rod 20 may have a semi-rigid, rigid or elastic configuration, and/or have elastic properties, such as the elastic properties corresponding to the material examples described above. In some embodiments, longitudinal rod 20 provides a selective amount of expansion and/or extension in an axial direction along length l. In some embodiments, longitudinal rod 20 has a flexible configuration, which includes movement in a lateral or side to side direction and prevents expanding and/or extension in an axial direction upon fixation with vertebrae. In some embodiments, longitudinal rod 20 may be compressible in an axial direction. Longitudinal rod 20 can include a plurality of separately attachable or connectable portions or sections, or may be monolithically formed as a single continuous element. System 10 can include one or a plurality of longitudinal rods 20. In some embodiments, longitudinal rod 20 is configured to extend over a plurality of vertebral levels.

In some embodiments, longitudinal rod 20 can have a uniform thickness/diameter. In some embodiments, longitudinal rod 20 may have various surface configurations, such as, for example, rough, threaded for connection with surgical instruments, arcuate, undulating, porous, semi-porous, dimpled, polished and/or textured. In some embodiments, the thickness defined by longitudinal rod 20 may be uniformly increasing or decreasing, or have alternate diameter dimensions along its length. In some embodiments, longitudinal rod 20 may have various cross section configurations, such as, for example, oval, oblong, triangular, rectangular, square, polygonal, irregular, uniform, non-uniform, variable and/or tapered.

Pedicle screws 30 are configured for engagement with concave side CA to attach longitudinal rod 20 with vertebrae V, as described herein. Pedicle screw 30 comprises a capture element, such as, for example, a receiver 32 including spaced apart arms 34, 36. Receiver 32 includes an inner surface 38. In some embodiments, arm 34 and/or arm 36 may be disposed at alternate orientations, such as, for example, transverse, perpendicular and/or other angular orientations such as acute or obtuse, co-axial and/or may be offset or staggered. In some embodiments, the outer surfaces of arms 34, 36 may include a recess or cavity configured to receive an insertion tool, compression instrument and/or instruments for inserting and tensioning pedicle screw 30.

Pedicle screw 30 includes a portion, such as, for example, a tissue penetrating shaft 46 extending between an end 48 and an end 50 along a longitudinal axis X2. Shaft 46 has a cylindrical cross section configuration that extends to a pointed distal tip. Shaft 46 includes an outer surface having an external threaded form. In some embodiments, the thread form on the outer surface of shaft 46 may include a single thread turn or a plurality of discrete threads. In some embodiments, other engaging structures may be located on shaft 46, such as, for example, a nail configuration, barbs, expanding elements, raised elements and/or spikes to facilitate engagement of shaft 46 with vertebral tissue.

In some embodiments, all or only a portion of shaft 46 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 46 may include one or a plurality of openings. In some embodiments, all or only a portion of the outer surface of shaft 46 may have alternate surface configurations to enhance fixation with tissue such as, for example, rough, arcuate, undulating, mesh, porous, semi-porous, dimpled and/or textured. In some embodiments, all or only a portion of shaft 46 may be disposed at alternate orientations, relative to receiver 32, such as, for example, transverse, perpendicular and/or other angular orientations such as acute or obtuse, co-axial and/or may be offset or staggered. In some embodiments, all or only a portion of shaft 46 may be cannulated.

End 48 of shaft 46 is connected with receiver 32 via a pin hinge such that receiver 32 is rotatable and/or pivotable relative to shaft 46 within a single plane, in the direction shown by arrows C in FIG. 3. In some embodiments, receiver 32 is rotatable relative to shaft 46 and vertebrae V in a transverse plane TP, as shown in FIG. 1. In some embodiments, pedicle screw 30 is configured to facilitate movement of longitudinal rod 20 and pedicle screw 30 in superior and/or inferior directions. In some embodiments, pedicle screw 30 is configured to limit movement of longitudinal rod 20 in anterior and/or posterior directions. In some embodiments, pedicle screw 30 comprises a fixed axis and/or a uni-axial fastener.

Inner surface 38 of each receiver 32 defines a cavity, such as, for example, a portion of a guide passageway 40. A plurality of receivers 32 form guide passageway 40 along concave side CA. Guide passageway 40 is configured for disposal of longitudinal rod 20. Guide passageway 40 guides movement of receivers 32 along and relative to longitudinal rod 20 during growth of vertebrae V. In some embodiments, with pedicle screws 30 attached to the vertebral levels of vertebrae V and as vertebrae V grows, receivers 32 move axially, rotatably and/or pivotally relative to longitudinal rod 20 to facilitate movement, rotation and/or flexibility of longitudinal rod 20 in coronal plane CP and resist and/or prevent movement, rotation and/or flexibility of longitudinal rod 20 in sagittal plane SP, as described herein. In some embodiments, guide passageway 40 is employed to resist and/or prevent movement of longitudinal rod 20 in coronal plane CP.

A fixation element, such as, for example, a set screw 70 is configured for threaded engagement with arms 34, 36 to dispose longitudinal rod 20 with receiver 32 in a non-locking configuration, as shown in FIG. 5. For example, longitudinal rod 20 is disposable with a portion of guide passageway 40 of a pedicle screw 30 and set screw 70 is fixed with receiver 32 to maintain longitudinal rod 20 with the pedicle screw 30 fastened at a particular vertebral level such that receiver 32 is movable, which includes axial, rotational and/or pivotable movement, relative to longitudinal rod 20. In some embodiments, longitudinal rod 20 is disposed with receiver 32 and rotatable and/or pivotable relative to shaft 46 and vertebrae V, in the direction shown by arrows D in FIG. 5, in a transverse plane TP, as shown in FIG. 1.

In some embodiments, surface 38 and longitudinal rod 20 define a gap G disposed about longitudinal rod 20. This configuration allows axial movement of longitudinal rod 20 relative to receiver 32 and vertebrae V. For example, longitudinal rod 20 is disposable with a portion of guide passageway 40 and pedicle screw 30, fastened at a particular vertebral level, are movable about and relative to longitudinal rod 20 as vertebrae V grows. As such, the spacing of gap G allows receivers 32 to move axially, rotatably and/or pivotally relative to longitudinal rod 20 to facilitate movement, rotation and/or flexibility of longitudinal rod 20 in coronal plane CP and resist and/or prevent movement, rotation and/or flexibility of longitudinal rod 20 in sagittal plane SP, as described herein. In some embodiments, set screw 70 is threaded with arms 34, 36 and engages longitudinal rod 20 to fix longitudinal rod 20 with receiver 32 in a locking configuration such that axial movement of pedicle screws 30 relative to longitudinal rod 20 is resisted and/or prevented.

In some embodiments, inner surface 38 may be disposed with the setscrew in alternate fixation configurations, such as, for example, friction fit, pressure fit, locking protrusion/recess, locking keyway and/or adhesive. In some embodiments, all or only a portion of inner surface 38 may have alternate surface configurations to enhance fixation with the setscrew such as, for example, rough, arcuate, undulating, mesh, porous, semi-porous, dimpled and/or textured.

In assembly, operation and use, spinal correction system 10, similar to the systems and methods described herein, is employed with a surgical procedure, such as, for example, a correction treatment of an affected portion of a spine, for example, a correction treatment to treat adolescent idiopathic scoliosis and/or Scheuermann's kyphosis of a spine. In some embodiments, one or all of the components of spinal correction system 10 can be delivered or implanted as a pre-assembled device or can be assembled in situ. Spinal correction system 10 may be completely or partially revised, removed or replaced.

In use, to treat a selected section of vertebrae V, as shown in FIGS. 1, 2 and 5, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Screws 18 are delivered along the surgical pathway to a surgical site adjacent to convex side CX of vertebrae V. Screws 18 are inserted or otherwise engaged and attached with the vertebral levels of convex side CX. Tether 12 is delivered along the surgical pathway to a surgical site adjacent convex side CX. Tether 12 is fixed with screws 18. In this configuration, tether 12 is attached with convex side CX to prevent growth of a selected section of vertebrae V, while allowing for growth and adjustments to concave side CA of vertebrae V to provide treatment. In some embodiments, compression of vertebrae V occurs along convex side CX.

Pedicle screws 30 are delivered along the surgical pathway to the surgical site adjacent to concave side CA. Screws 30 are inserted or otherwise engaged and attached with the vertebral levels of concave side CA. Longitudinal rod 20 is delivered along the surgical pathway to a surgical site adjacent concave side CA. Longitudinal rod 20 is disposed with guide passageway 40 of receivers 32. Receivers 32 are movable, rotatable and/or pivotable in transverse plane TP, as described herein, and for example, as shown in the direction of arrows D in FIG. 5, to receive longitudinal rod 20. In some embodiments, longitudinal rod 20 includes a pre-selected curvature having a selected kyphotic curve, which may include curvature in sagittal plane SP.

Set screw 70 is threaded with arms 34, 36 of receivers 32 to dispose longitudinal rod 20 in a non-locking configuration with pedicle screws 30, as shown in FIGS. 1, 2 and 5. A set screw 70a is engaged with a pedicle screw 30a fastened with a vertebral level adjacent an apical portion AP of vertebrae V to fix longitudinal rod 20 in a locking configuration with pedicle screw 30a such that axial movement of pedicle screw 30a relative to longitudinal rod 20 is resisted and/or prevented.

Longitudinal rod 20 is disposed with guide passageway 40, which guides movement of receivers 32 along and relative to longitudinal rod 20 during growth of vertebrae V. Pedicle screws 30 are attached to the vertebral levels of concave side CA and as vertebrae V grows, receivers 32 move axially, rotatably and/or pivotally relative to longitudinal rod 20 to facilitate movement, rotation and/or flexibility of longitudinal rod 20 in coronal plane CP and resist and/or prevent movement, rotation and/or flexibility of longitudinal rod 20 in sagittal plane SP, as described herein.

Upon completion of the procedure, the surgical instruments, assemblies and non-implanted components of spinal correction system 10 are removed from the surgical site and the incision is closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10.

In some embodiments, spinal correction system 10 may include one or a plurality of tethers, rods, plates, connectors and/or bone fasteners for use with a single vertebral level or a plurality of vertebral levels. In some embodiments, one or more bone fasteners may be engaged with tissue in various orientations, such as, for example, series, parallel, offset, staggered and/or alternate vertebral levels. In some embodiments, one or more of bone fasteners may comprise multiaxial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts In some embodiments, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 may be used to prevent or minimize curve progression in individuals of various ages.

Figure 6:
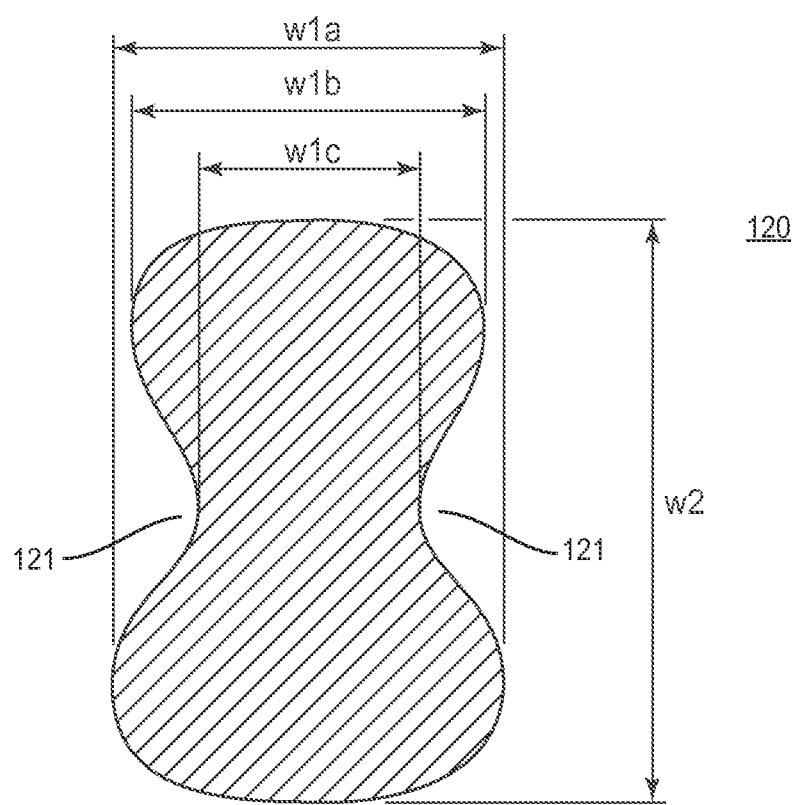
FIG. 6 is cross-section view of one embodiment of a component of a surgical system in accordance with the principles of the present disclosure.
Figure 7:
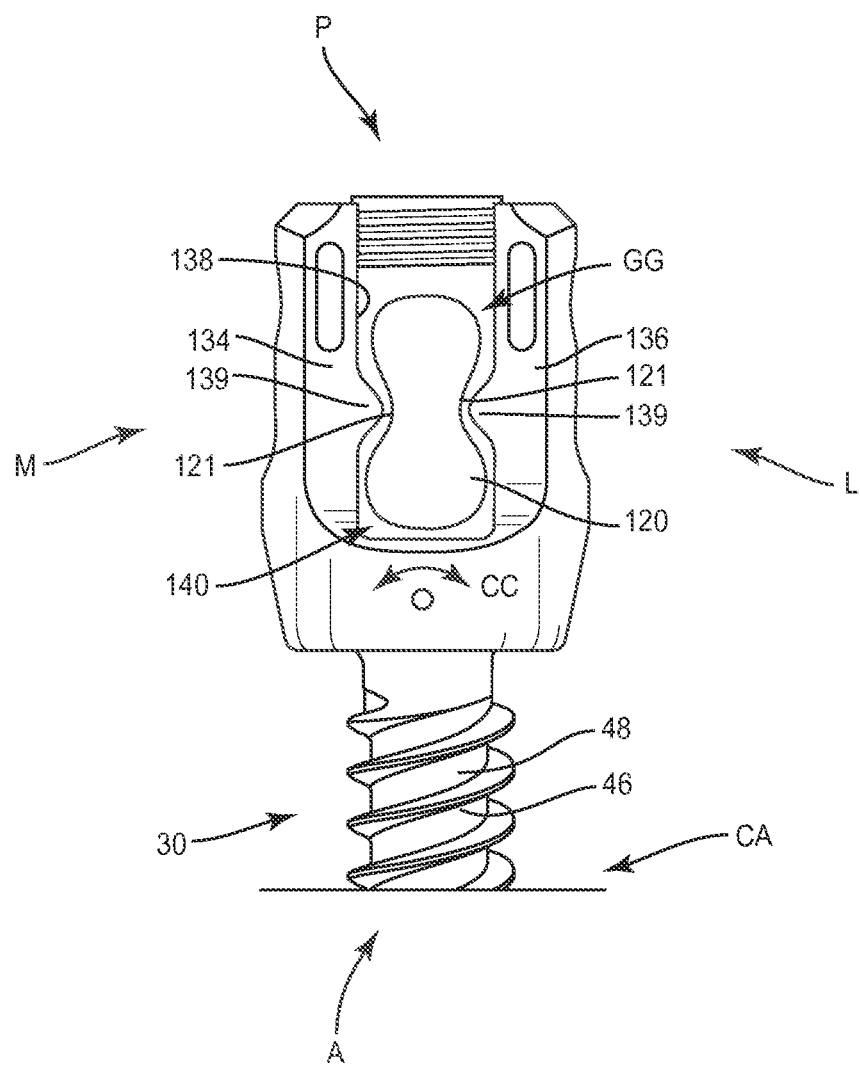
FIG. 7 is a plan view of one embodiment of components of a surgical system in accordance with the principles of the present disclosure disposed with vertebrae.

In one embodiment, as shown in FIGS. 6 and 7, spinal correction system 10, similar to the systems and methods described herein, includes a longitudinal rod 120, similar to longitudinal rod 20 described with regard to FIGS. 1-5. Longitudinal rod 120 has a cross-section having enlarged widths w1a, w1b, w2 and a reduced dimension width w1c, as shown in FIG. 6. Width w1c defines channels 121 along the length of longitudinal rod 120. Longitudinal rod 120 is connected with concave side CA, as shown in FIG. 7, and widths w1a, w1b, w1c extend medial M-lateral L and width w2 extends anterior A-posterior P relative to vertebrae V. The cross-section configuration of longitudinal rod 120 is configured to resist and/or prevent movement, rotation and/or flexibility of longitudinal rod 120 in coronal plane CP (FIG. 2) and sagittal plane SP (FIG. 1).

Pedicle screw 30 comprises a capture element, such as, for example, a receiver 132, similar to receiver 32 described herein. Receiver 132 includes spaced apart arms 134, 136. Receiver 132 includes an inner surface 138. Surface 138 includes protrusions 139 disposable within channels 121. End 48 of shaft 46 is connected with receiver 132 via a pin hinge such that receiver 132 is rotatable and/or pivotable relative to shaft 46 within a single plane, such as, for example, transverse plane TP (FIG. 1), in the direction shown by arrows CC in FIG. 7.

Inner surface 138 of each receiver 132 defines a portion of a guide passageway 140, similar to passageway 40 described herein. Set screw 70 is configured for threaded engagement with arms 134, 136 to dispose longitudinal rod 120 with receiver 132 in a non-locking configuration, as shown in FIG. 7. For example, longitudinal rod 120 is disposable with a portion of guide passageway 140 of a pedicle screw 30 and set screw 70 is fixed with receiver 132 to maintain longitudinal rod 120 with the pedicle screw 30 fastened at a particular vertebral level such that receiver 132 is movable, which includes axial, rotational and/or pivotable movement, relative to longitudinal rod 120.

In some embodiments, surface 138 and longitudinal rod 120 define a gap GG disposed about longitudinal rod 120. This configuration allows axial movement of longitudinal rod 120 relative to receiver 132 and vertebrae V. For example, longitudinal rod 120 is disposable with a portion of guide passageway 140 and pedicle screw 30, fastened at a particular vertebral level, are movable about and relative to longitudinal rod 120 as vertebrae V grows.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
a first member configured for attachment to a first portion of vertebral tissue that defines a longitudinal axis; and
a second member that is detached from the first member and configured for attachment to a second portion of the vertebral tissue such that the second portion is axially movable relative to the second member and sagittal movement of the second member relative to the second portion is resisted and/or prevented.

2. A spinal construct as recited in claim 1, wherein the first member includes a tether and the first portion comprises a convex side of vertebrae.

3. A spinal construct as recited in claim 1, wherein the second member includes a growth rod and the second portion comprises a concave side of vertebrae.

4. A spinal construct as recited in claim 1, wherein the second member is coronally moveable relative to the second portion.

5. A spinal construct as recited in claim 1, wherein coronal movement of the second member relative to the second portion is resisted and/or prevented.

6. A spinal construct as recited in claim 1, wherein the second member has a pre-selected curvature.

7. A spinal construct as recited in claim 1, wherein the second member has a pre-selected sagittal curvature of thoracic vertebrae.

8. A spinal construct as recited in claim 1, wherein the second member has a cross section comprising an anterior-posterior oriented dimension that is greater than a medial-lateral oriented dimension.

9. A spinal construct as recited in claim 1, further comprising at least one bone fastener engageable with the second portion and including a capture element.

10. A spinal construct as recited in claim 9, further comprising at least one fixation element engageable with the second portion and disposed in fixed relation with the second member.

11. A spinal construct as recited in claim 1, further comprising at least one bone fastener engaged with the second portion, the at least one bone fastener including a shaft for penetrating the second portion and a capture element that is rotatable relative to the shaft.

12. A spinal construct as recited in claim 1, further comprising at least one bone fastener engageable with the second portion and including an inner surface that defines an implant cavity for disposal of the second member, the second member being engageable with the inner surface to resist and/or prevent rotation of the second member relative to the inner surface.

13. A spinal construct as recited in claim 1, further comprising a plurality of bone fasteners engageable with the second portion and the second member having a pre-selected curvature such that the bone fasteners comprise a guide passageway for disposal of the second member.

14. A spinal construct as recited in claim 1, wherein the second portion is axially translatable and rotatable relative to the second member.

15. A spinal construct comprising:
a first member configured for attachment to a convex side of vertebrae that defines a sagittal plane and a coronal plane; and
a second member that is disconnected from the first member, the second member having a pre-selected curvature and being configured for attachment to a concave side of the vertebrae such that the second member is movable along the coronal plane relative to the concave side and movement of the second member relative to the concave side along the sagittal plane is resisted and/or prevented.

16. A spinal construct as recited in claim 15, further comprising at least one bone fastener engageable with the concave side and including a capture element.

17. A spinal construct as recited in claim 15, further comprising at least one bone fastener engaged with the concave side, the at least one bone fastener including a shaft for penetrating the concave side and a capture element that is rotatable relative to the shaft.

18. A spinal construct as recited in claim 15, further comprising a plurality of bone fasteners engageable with the concave side such that the bone fasteners comprise a guide passageway for the pre-selected curvature.

19. A spinal construct as recited in claim 15, wherein the pre-selected curvature comprises a sagittal curvature of thoracic vertebrae.

20. A spinal correction system comprising:
a tether configured for attachment to a convex side of vertebrae that defines a longitudinal axis; a plurality of bone fasteners configured for attachment to a concave side of the vertebrae; and
a growth rod that is non-continuous with the tether and configured for disposal with the bone fasteners such that the concave side is axially movable relative to the growth rod and sagittal movement of the growth rod relative to the concave side is resisted and/or prevented.

* * * * *